United States Patent [19]
Arnold et al.

[11] Patent Number: 5,955,041
[45] Date of Patent: Sep. 21, 1999

[54] NATURAL CIRCULATION REACTOR AND USE FOR PRODUCING LINEAR AND CYCLIC ACETALS

[75] Inventors: Dieter Arnold, Königstein; Bernhard Hierholzer, Frankfurt; Hubert Wloch, Niedernhausen; Karl-Friedrich Mück, Wiesbaden, all of Germany

[73] Assignee: Hoechst AG, Frankfurt, Germany

[21] Appl. No.: 08/534,550

[22] Filed: Sep. 27, 1995

[30] Foreign Application Priority Data

Sep. 29, 1994 [DE] Germany .............................. 44 34 845

[51] Int. Cl.⁶ .............................. F28D 8/04; B01D 3/02; C07D 323/06
[52] U.S. Cl. .......................... 422/198; 422/205; 422/227; 422/228; 422/230; 202/153; 202/158; 202/156; 202/182; 202/239; 202/DIG. 6; 549/368; 549/369
[58] Field of Search ..................... 422/198, 205, 422/227, 228, 230; 202/153, 158, 156, 182, 239, DIG. 6; 549/368, 369

[56] References Cited

U.S. PATENT DOCUMENTS

| | | |
|---|---|---|
| 3,697,546 | 10/1972 | Asakawa et al. . |
| 4,340,542 | 7/1982 | Bär et al. ................................. 549/368 |
| 4,493,752 | 1/1985 | Naito et al. ................................ 203/71 |
| 4,504,670 | 3/1985 | Voigt et al. .............................. 549/347 |
| 4,946,561 | 8/1990 | Braun et al. .............................. 203/49 |
| 5,508,448 | 4/1996 | Emig et al. .............................. 549/368 |

FOREIGN PATENT DOCUMENTS

| | | |
|---|---|---|
| 0017067 | 3/1980 | European Pat. Off. . |
| 0028361 | 5/1981 | European Pat. Off. . |
| 0012304 | 6/1990 | European Pat. Off. . |
| 146-148 | 9/1979 | Germany . |

OTHER PUBLICATIONS

Derwent Abstract No. DT 2853–091 published Dec. 8, 1978.
Derwent Abstract No. DT 2912–767 published Mar. 30, 1979.
Derwent Abstract No. EP 28–361 published Oct. 31, 1979.
Derwent Abstract No. DD 146–148 published Sep. 18, 1979.
W. Foert (Arsg). "Ullmanns Encycklopadie der technischen Chemie, 3. Auflag, 1, Band: Chemischer Apparatebau und Ferfahrenstechnik" 1951, Urban & Schwarzenberg, Munchen–Berlin X P002018369.

*Primary Examiner*—Glenn Caldarola
*Attorney, Agent, or Firm*—Frommer Lawrence & Haug LLP

[57] ABSTRACT

This invention relates to a reactor 1 for the continuous production of linear or cyclic acetals, in particular trioxane, dioxolane, tetroxane, dimethoxymethane, diethoxymethane, diethoxyethane and dibutoxyethane. This reactor has internal adjacently arranged evaporator elements 2, which allow for flow-through of a heat transport medium, and which are at least two meters high so as to generate a thermosiphon flow. The clear cross section between the evaporator elements is 20 to 80% of the overall cross section. Using the reactor, circulation ratios of up to 250 can be achieved. Thus, the reliability and availability of a production plant is increased while the susceptibility to breakdown decreases.

18 Claims, 3 Drawing Sheets

NATURAL CIRCULATION REACTOR AND USE FOR PRODUCING LINEAR AND CYCLIC ACETALS

The invention relates to a reaction vessel having internally arranged evaporator elements and its use in the production of linear or cyclic acetals.

BACKGROUND OF THE INVENTION

Reaction vessels of the said type are known and are used in many processes in the chemical industry.

The internally arranged evaporator elements are conventionally constructed in the form of plates, pipe coils, tube bundles or other tubular constructions, a heat transport medium flowing through the plates or tubes which gives off heat via the plates or tube wall to a reaction medium in the reaction vessel or absorbs heat from this. If intensive mixing of the reaction medium is necessary for certain reactions, the convection which the said tubular constructions generate is frequently insufficient and the reaction medium must additionally be mixed by mechanical means, for example via an agitator or via an external circulation pump. An apparatus having such an external circulation is disclosed by EP 0 012 304, in which a process and an apparatus for the continuous preparation of trioxane are described. In this process the trioxane is formed from aqueous formaldehyde in the presence of acid catalysts at elevated temperatures and is separated off from the reaction mixture by distillation. An external forced circulation is responsible for the intensive mixing of the reaction mixture.

A measure of the efficacy of this forced circulation which can be used in this process is the circulation ratio which is defined as the ratio of the amount of liquid circulating, in kg/s, to the amount of liquid evaporated, in kg/s. In the production of trioxane, a circulation ratio greater than 50 is to be sought after, which previously could only be achieved via such an external forced circulation. However, for this, the installation of cost-intensive and high-maintenance apparatuses, pumps and pipes is necessary, which additionally hold safety hazards.

The object of the invention is to improve a reactor of the type mentioned at the outset in such a manner that a sufficient mixing of the reaction medium is possible even without additional mechanical means.

SUMMARY OF THE INVENTION

According to the invention this is achieved by the fact that the evaporator elements are at least two meters high to generate a thermosiphon flow and the clear cross section between the evaporator elements is 20 to 80% of the overall cross section.

Further embodiments of the invention are given by claims 2 to 8.

The novel reaction vessel as claimed in claim 1 is suitable for preparing linear or cyclic acetals, in particular trioxane, dioxolane, tetroxane, dimethoxymethane, diethoxymethane, diethoxyethane and dibutoxyethane.

Circulation ratios up to 250 can be achieved using the novel reactor, the reliability and the availability of the production plant being increased at the same time as the susceptibility to breakdown decreases.

BRIEF DESCRIPTION OF THE DRAWINGS

Three illustrative examples of the invention are described in more detail below on the basis of the drawings according to FIGS. 1 to 3. In the drawings FIG. 1 diagrammatically shows a first embodiment of the invention in sectional view, FIG. 2 diagrammatically shows a second embodiment of the invention having evaporator elements arranged conically to each other in section view, FIG. 3 diagrammatically shows a third embodiment of the invention having a box-shaped attachment in sectional view.

DETAILED DESCRIPTION OF THE INVENTION

Figure 1:
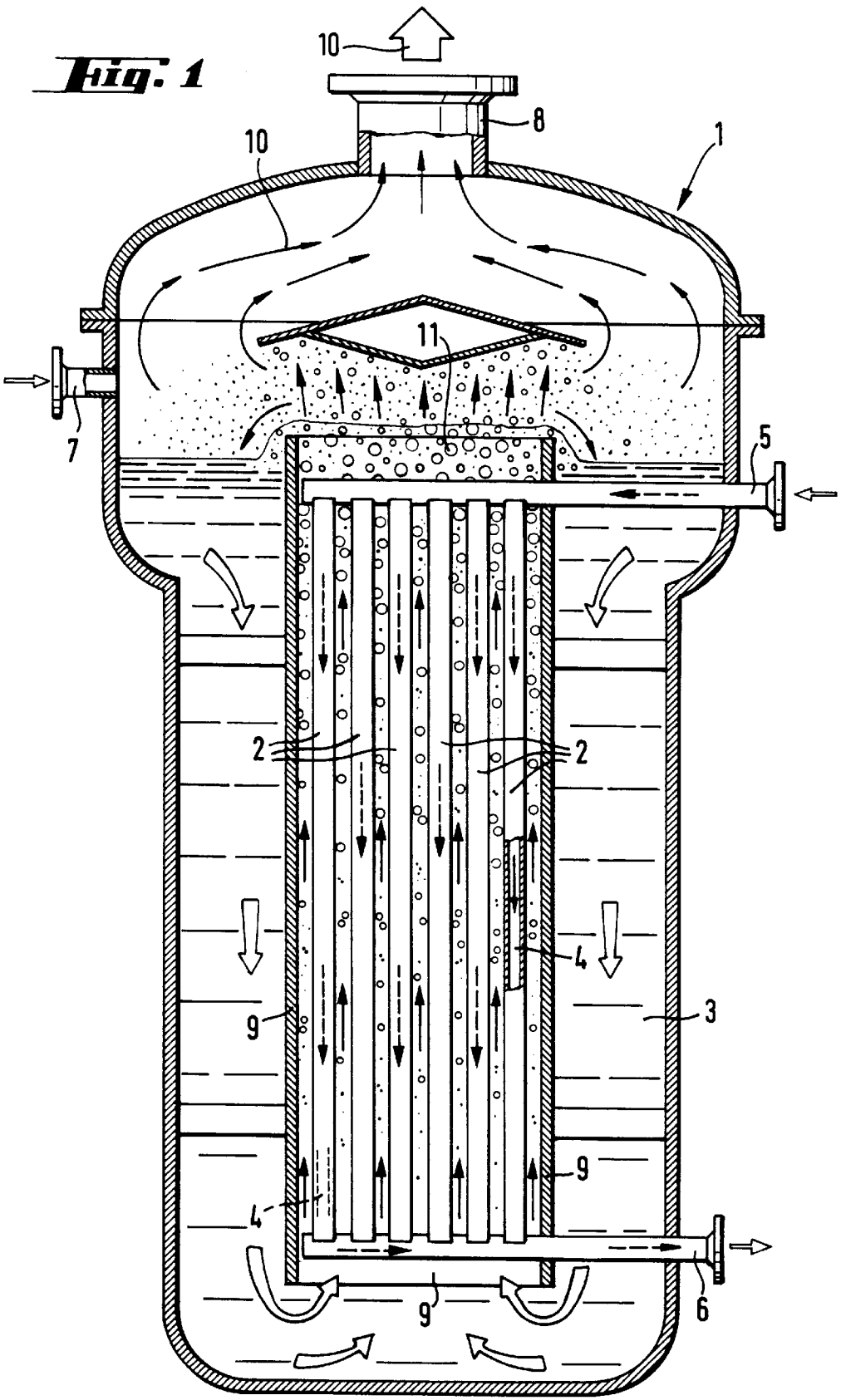

In a vertically upright reaction vessel shown in FIG. 1, in the preparation of trioxane, formaldehyde partially reacts in the presence of acids in a liquid medium 3 to give trioxane. This trioxane is recovered by evaporating the medium 3 to give a vapor 10 and is taken off with the vapor 10 via an outlet 8. The reaction starting materials are added via a feed 7.

Since, as a consequence of the evaporation, trioxane is depleted in a zone of the medium 3 close to the surface, if a trioxane yield as high as possible is to be achieved, the medium 3 must be intensively mixed so that the trioxane concentration in the zone close to the surface is as near as possible to the thermodynamic equilibrium concentration of vapor 10/medium 3. This is best achieved by letting the medium 3 circulate.

According to the invention this is achieved by the fact that evaporator elements 2, which are preferably constructed as plates, are arranged vertically and parallel to each other in the interior of the reactor. These plates 2 have cavities 4 through which a heat transport medium, in particular heating steam, can flow. They are also termed heat-transfer sheets and if required can also be used for cooling. The heat transport medium enters via a feed 5 and exits via an outlet 6.

If the plates 2 are heated, the medium 3 rises upwards between the plates, reinforced by vapor bubbles which form depending on the process conditions. In this manner, in accordance with the thermosiphon principle, a circulating flow is generated—a thermosiphon flow—which ensures the required circulation, circulation ratios greater than 50 being possible. For this purpose, the plates 2 must be at least 2 m high and the clear cross section between the plates 2 must be between 20 and 80%, preferably between 30 and 70%, of the overall cross section, the overall cross section being defined as the sum of the clear cross section between the plates and cross section of the plates 2.

The hydraulic pressure drop which is caused by the totality of the plates 2 may not exceed 250 mbar in the example described.

Figure 2:
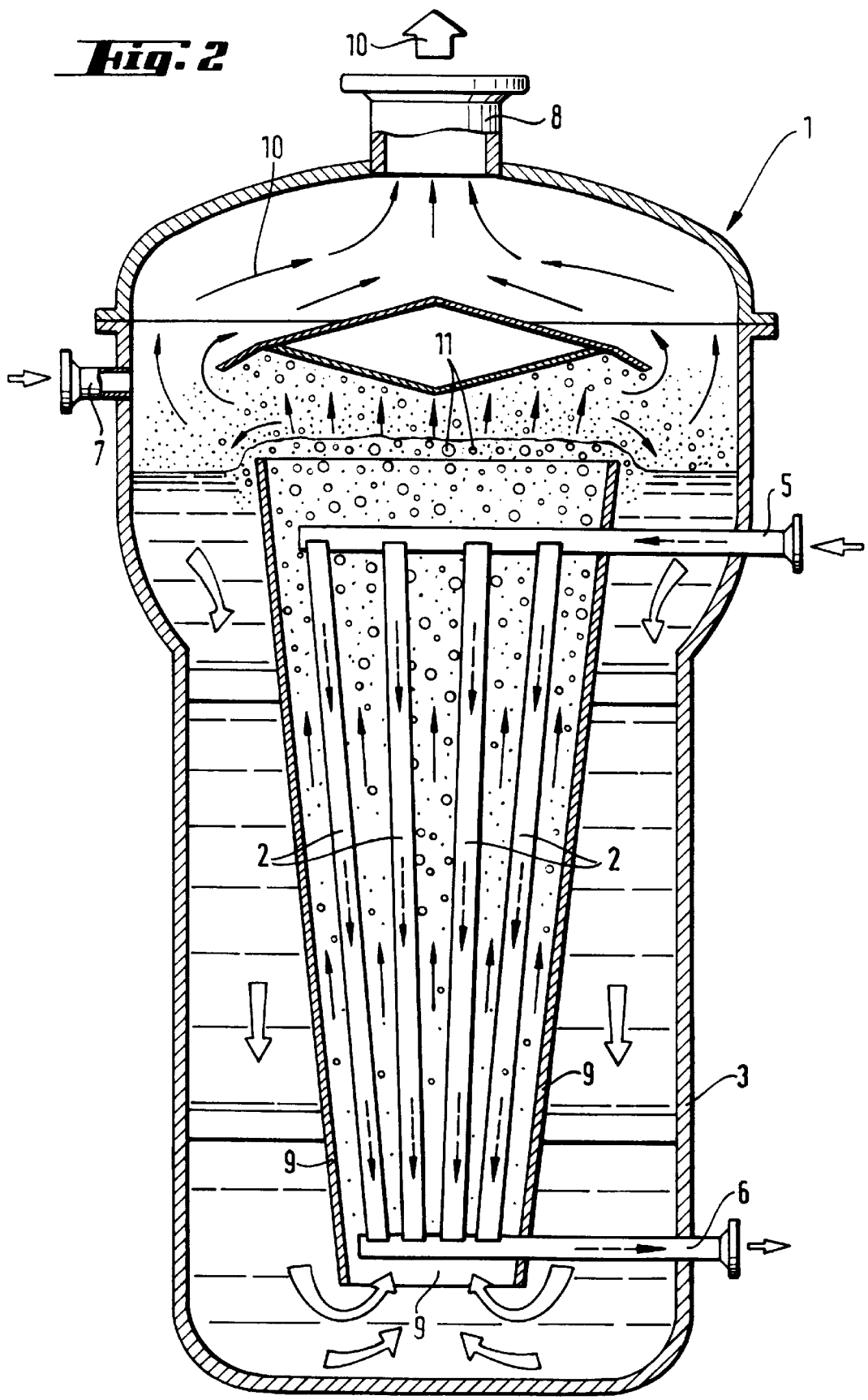

To separate the ascending flow from the descending flow, sheets 9 are arranged vertically around the plates 2. During heating, if vapor bubbles 11 form on the surfaces of the plate 2, it is advantageous to arrange the plates conically to each other, as shown in FIG. 2, at a preset angle between 0 and 15°, preferably between 3 and 5°, by which means the distance between the plates increases from bottom to top. This decreases the hydraulic resistance of the space between the plates 2 from bottom to top and thus the volume increase of the vapor/liquid mixture rising upwards is taken into account.

Figure 3:
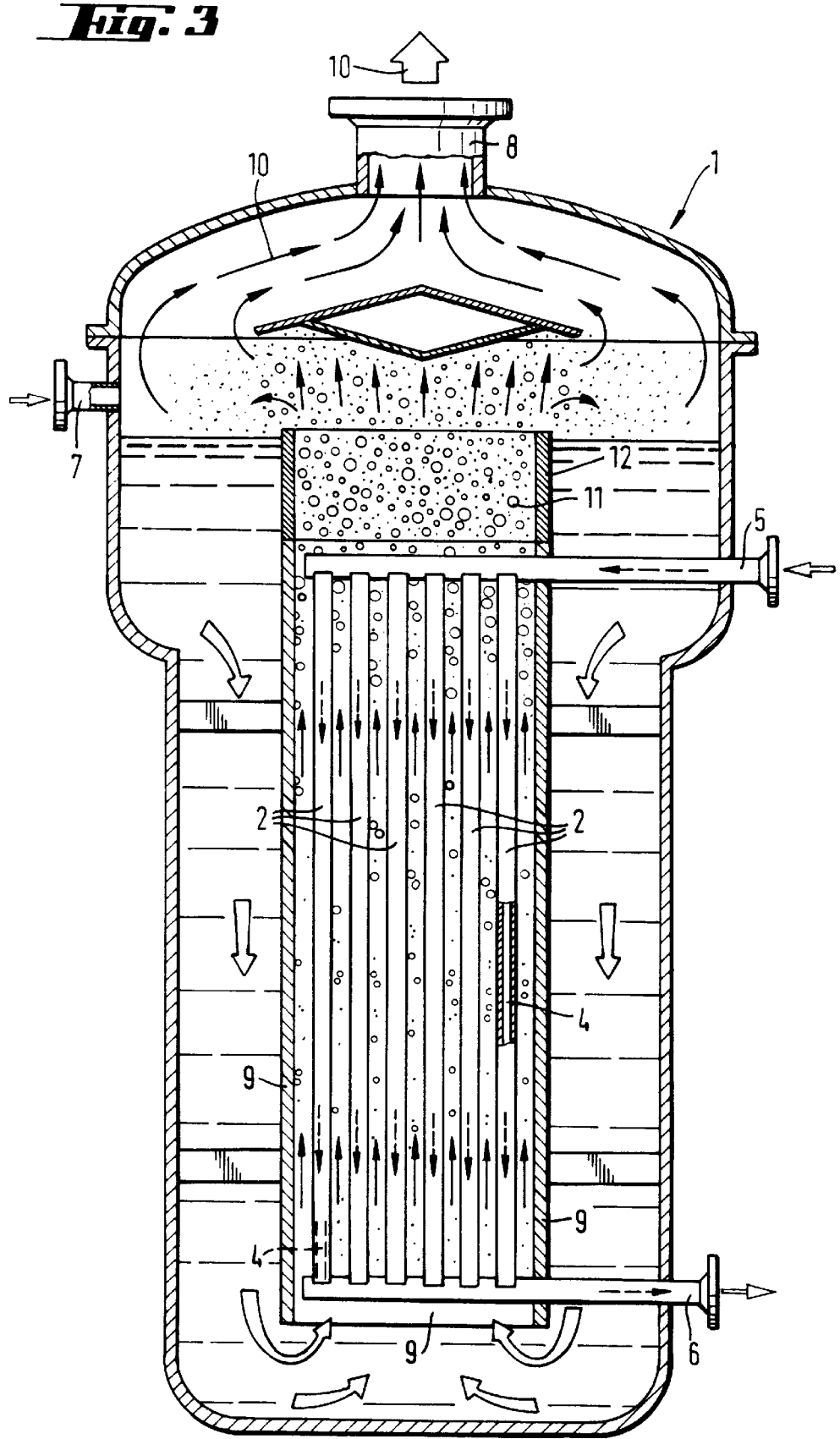

In a particularly advantageous embodiment of the novel reactor, a frame-shaped attachment 12 is arranged over the evaporator elements (FIG. 3). The attachment 12 seals laterally tightly to the sheets 9, so that in the operating state a higher liquid level can form outside the attachment 12 than inside. The height of the attachment preferably comprises the range from 0.1 to 0.8 m. The differing liquid levels and the pressure gradients caused by this further increase the circulation ratio.

Furthermore, it is advantageous to polish the medium-contacting surfaces of the plates 2, since this likewise decreases the hydraulic resistance.

Materials for reactor 1 and plates 2 which are preferably used are steel or stainless and acid-resistant steels or special materials.

The advantages of the novel reactor are further illustrated below on the basis of examples.

In a pilot plant, trioxane was produced using four different reactors: a natural circulation reactor having external circulation and externally arranged heating elements (A), a reactor having forced circulation (B), a novel reactor corresponding to FIG. 1 (C) and a novel reactor corresponding to FIG. 3 (D). The circulation ratios achieved are recorded in the table below, together with the trioxane concentration achieved in the vapor (in % by weight of the equilibrium concentration).

|  | Reactor | Circulation ratio | Trioxane concentration in vapor |
|---|---|---|---|
| Prior | A | 20–50 | 82.9–92.2 |
| Art | B | 80–110 | 95.1–96.6 |
| Invention | C | 155–185 | 97.5–98.0 |
|  | D | 220–250 | 98.0–98.5 |

We claim:

1. A reactor for the continuous production of linear or cyclic acetals, said reactor having evaporator elements for generating a thermosiphon flow, the improvement which comprises the evaporator elements being arranged internally within the reactor and conically to each other at an angle of between 0° and 15° relative to each other so that the distance between adjacent plates increases from bottom to top and having a clear cross section between the evaporator elements that is about 20 to 80% of the overall cross section; the overall cross section being the sum of the clear cross section between the evaporator elements and the cross section of the evaporator elements.

2. The reactor as claimed in claim 1, wherein the evaporator elements (2) are heat-transfer sheets.

3. The reactor as claimed in claim 1, wherein the evaporator elements (2) are fabricated from a material selected from the group consisting of steel, a corrosion-resistant metal, and a corrosion-resistant alloy.

4. The reactor as claimed in claim 1, wherein the outer surface of the evaporator elements (2) is polished.

5. The reactor as claimed in claim 1, wherein metal sheets (9) are arranged vertically around the evaporator elements (2).

6. The reactor as claimed in claim 1, wherein an attached frame (12) is arranged over the evaporator elements (2).

7. The reactor as claimed in claim 1 in which the clear cross section between the evaporator elements is about 30 to 70% of the overall cross section, the overall cross section being the sum of the clear cross section between the evaporator elements and the cross section of the evaporator elements.

8. A reactor for the continuous production of linear or cyclic acetals, said reactor having evaporator elements for generating a thermosiphon flow, the improvement which comprises the evaporator elements being arranged internally and adjacently within the reactor, having a clear cross section between the evaporator elements that is about 20 to 80% of the overall cross section, the overall cross section being the sum of the clear cross section between the evaporator elements and the cross section of the evaporator elements, and wherein an attached frame is arranged over the evaporator elements.

9. The reactor as claimed in claim 8, wherein the evaporator elements (2) are arranged conically to each other at an angle of between 0° to 15° relative to each other so that the distance between adjacent plates increases from bottom to top.

10. The reactor as claimed in claim 8, wherein the evaporator elements (2) are heat-transfer sheets.

11. The reactor as claimed in claim 8, wherein the evaporator elements (2) are fabricated from a material selected from the group consisting of steel, a corrosion-resistant metal, and a corrosion-resistant alloy.

12. The reactor as claimed in claim 8, wherein the outer surface of the evaporator elements (2) is polished.

13. The reactor as claimed in claim 8, wherein metal sheets (9) are arranged vertically around the evaporator elements (2).

14. The improved reactor as claimed in claim 8 in which the clear cross section between the evaporator elements is about 30 to 70% of the overall cross section, the overall cross section being the sum of the clear cross section between the evaporator elements and the cross section of the evaporator elements.

15. A method for the production of linear or cyclic acetals comprising placing the reactants into a reactor having generating elements for generating a siphon flow and reacting said reactants under conditions sufficient to produce linear or cyclic acetals the improvement which comprises using a reactor where the evaporator elements being arranged internally within the reactor and conically to each other at an angle of between 0° and 15° relative to each other so that the distance between adjacent plates increases from bottom to top and having a clear cross section between the evaporator elements that is about 20 to 80% of the overall cross section, the overall cross section being the sum of the clear cross section between the evaporator elements and the cross section of the evaporator elements.

16. The method as claimed in claim 15 wherein the linear or cyclic acetals are selected from the group consisting of trioxane, dioxolane, tetroxane, dimethoxymethane, diethoxymethane, diethoxyethane and dibutoxyethane.

17. A method for the production of linear or cyclic acetals comprising placing the reactants into a reactor having generating elements for generating a siphon flow and reacting said reactants under conditions sufficient to produce linear or cyclic acetals the improvement which comprises using a reactor where the evaporator elements being arranged internally and adjacently within the reactor, having a clear cross section between the evaporator elements that is about 20 to 80% of the overall cross section, the overall cross section being the sum of the clear cross section between the evaporator elements and the cross section of the evaporator elements, and wherein an attached frame is arranged over the evaporator elements.

18. The method as claimed in claim 17 wherein the linear or cyclic acetals are selected from the group consisting of trioxane, dioxolane, tetroxane, dimethoxymethane, diethoxymethane, diethoxyethane and dibutoxyethane.

* * * * *